US00PP21331P2

(12) United States Plant Patent
Verwer

(10) Patent No.: US PP21,331 P2
(45) Date of Patent: Sep. 28, 2010

(54) ***DAHLIA* PLANT NAMED 'KARMA FIESTA'**

(50) Latin Name: *Dahlia hybrida*
Varietal Denomination: Karma Fiesta

(75) Inventor: Aad W. M. Verwer, Lisse (NL)

(73) Assignee: Verwer Dahlia's B.V., Lisse (NL)

( * ) Notice: Subject to any disclaimer, the term of this patent is extended or adjusted under 35 U.S.C. 154(b) by 0 days.

(21) Appl. No.: 12/386,664

(22) Filed: Apr. 20, 2009

(51) Int. Cl.
*A01H 5/00* (2006.01)

(52) U.S. Cl. ..... Plt./321
(58) Field of Classification Search ..... Plt./321
See application file for complete search history.

*Primary Examiner*—Annette H Para
(74) *Attorney, Agent, or Firm*—C. A. Whealy

(57) ABSTRACT

A new and distinct cultivar of *Dahlia* plant named 'Karma Fiesta', characterized by its upright plant habit; deeply serrated foliage; freely flowering habit; strong and erect peduncles; decorative-type inflorescence form; large inflorescences with yellow and orange bi-colored ray florets; and good postproduction longevity.

2 Drawing Sheets

Botanical designation: *Dahlia hybrida.*
Cultivar denomination: 'Karma Fiesta'.

BACKGROUND OF THE INVENTION

The present invention relates to a new and distinct cultivar of *Dahlia* plant, botanically known as *Dahlia hybrida*, and hereinafter referred to by the name 'Karma Fiesta'.

The new *Dahlia* plant is a product of a planned breeding program conducted by the Inventor in Lisse, The Netherlands. The objective of the breeding program is to create new cut flower *Dahlia* cultivars that have a freely flowering habit, decorative inflorescence form, attractive ray floret coloration and good postproduction longevity.

The new *Dahlia* plant originated from a cross-pollination conducted by the Inventor in Lisse, The Netherlands during the summer of 2003 of a proprietary seedling selection of *Dahlia hybrida* identified as code number VD4-76, not patented, as the female, or seed, parent with *Dahlia hybrida* 'Karma Irene', disclosed in U.S. Plant Pat. No. 18,406, as the male, or pollen, parent. The new *Dahlia* was discovered and selected by the Inventor as a single flowering plant within the progeny of the stated cross-pollination in a controlled greenhouse environment in Lisse, The Netherlands during the summer of 2004.

Asexual reproduction of the new *Dahlia* by cuttings since the spring of 2007 in a controlled greenhouse environment in Lisse, The Netherlands, has shown that the unique features of this new *Dahlia* are stable and reproduced true to type in successive generations.

SUMMARY OF THE INVENTION

Plants of the new *Dahlia* have not been observed under all possible environmental conditions. The phenotype may vary somewhat with variations in environment such as temperature and light intensity, without, however, any variance in genotype.

The following traits have been repeatedly observed and are determined to be the unique characteristics of 'Karma Fiesta'. These characteristics in combination distinguish 'Karma Fiesta' as a new and distinct cultivar of cut flower *Dahlia:*

1. Upright plant habit.
2. Deeply serrated foliage.
3. Freely flowering habit.
4. Strong and erect peduncles.
5. Decorative-type inflorescence form.
6. Large inflorescences with yellow and orange bi-colored ray florets.
7. Good postproduction longevity.

Plants of the new *Dahlia* differ primarily from plants of the female parent selection in the following characteristics:

1. Plants of the new *Dahlia* are shorter than plants of the female parent selection.
2. Plants of the new *Dahlia* are more freely branching than plants of the female parent selection.
3. Plants of the new *Dahlia* and the female parent selection differ in ray floret color as plants of the female parent selection have purple-colored ray florets.
4. Inflorescences of plants of the new *Dahlia* are longer lasting than inflorescences of plants of the female parent selection.

Plants of the new *Dahlia* differ primarily from plants of the male parent, 'Karma Irene', in the following characteristics:

1. Plants of the new *Dahlia* are more freely branching than plants of 'Karma Irene'.
2. Leaves of plants of the new *Dahlia* are more deeply serrated than leaves of plants of 'Karma Irene'.
3. Plants of the new *Dahlia* have larger inflorescences than plants of 'Karma Irene'.
4. Plants of the new *Dahlia* and 'Karma Irene' differ in ray floret color as plants of 'Karma Irene' have red orange-colored ray florets.

Plants of the new *Dahlia* can be compared to plants of the *Dahlia hybrida* 'Bridge View Aloha', not patented. In side-by-side comparisons conducted in Lisse, The Netherlands, plants of the new *Dahlia* differed from plants of 'Bridge View Aloha' in the following characteristics:

1. Plants of the new *Dahlia* were shorter than plants of 'Bridge View Aloha'.
2. Plants of the new *Dahlia* were denser than and not as open as plants of 'Bridge View Aloha'.

3. Plants of the new *Dahlia* had smaller inflorescences than plants of 'Bridge View Aloha'.

BRIEF DESCRIPTION OF THE PHOTOGRAPHS

The accompanying photographs illustrate the overall appearance of the new *Dahlia* plant. The photographs show the colors as true as it is reasonably possible to obtain in colored reproductions of this type.

Colors in the photographs may differ slightly from the color values cited in the detailed botanical description which accurately describe the colors of the new *Dahlia* plant.

The photograph on the first sheet comprises a side perspective view of typical flowering plants of 'Karma Fiesta' grown in an outdoor nursery.

The photograph on the second sheet is a close-up view of a typical open inflorescence and a typical opening inflorescence of 'Karma Fiesta'.

DETAILED BOTANICAL DESCRIPTION

The following observations and measurements describe plants grown in Lisse, The Netherlands during the summer and autumn in an outdoor nursery and under conditions and practices which approximate those generally used in commercial *Dahlia* production. During the production of the plants, day temperatures ranged from 14° C. to 30° C. and night temperatures ranged from 8° C. to 20° C. Plants were pinched one time about three to four weeks after planting. Measurements and numerical values represent averages for typical flowering plants. Plants used for the photographs were 13 weeks old and plants used for the description were three to four months old. In the following description, color references are made to The Royal Horticultural Society Colour Chart, 1995 Edition, except where general terms of ordinary dictionary significance are used.

Botanical classification: *Dahlia hybrida* 'Karma Fiesta'.

Parentage:

*Female, or seed, parent.*—Proprietary seedling selection of *Dahlia hybrida* identified as code number VD4-76, not patented.

*Male, or pollen, parent.*—*Dahlia hybrida* 'Karma Irene', disclosed in U.S. Plant Pat. No. 18,406.

Propagation:

Type: By vegetative cuttings.

*Time to initiate roots, summer.*—About seven to ten days at soil temperatures of 15° C.

*Time to initiate roots, winter.*—About eight to eleven days at soil temperatures of 15° C.

*Time to produce a rooted young plant, summer.*—About 15 days at soil temperatures of 15° C.

*Time to produce a rooted young plant, winter.*—About 16 to 17 days at soil temperatures of 15° C.

*Root description.*—Fine to medium in thickness, fleshy; color, close to 157B.

*Rooting habit.*—Moderately freely branching; moderately dense.

*Tubers.*—Length: About 20 cm. Diameter: About 15 cm. Color: Close to 200B.

Plant description:

*Plant form/growth habit.*—Upright plant habit; inverted triangle plant form; freely basal branching with about eight to ten lateral branches per plant; inflorescences held above the foliage on straight and strong peduncles; vigorous, bushy and dense growth habit.

*Plant height.*—About 110 cm.

*Plant diameter or spread.*—About 50 cm.

*Lateral branches.*—Length: About 80 cm. Diameter: About 1.1 cm to 3 cm. Internode length: About 5 cm to 23 cm. Texture: Smooth, glabrous. Color: Towards the base, close to 152A; towards the apex, tinted with close to 187A.

Foliage description:

*Arrangement.*—Leaves opposite; leaves may be single or compound with three or five leaflets.

*Shape.*—Ovate.

*Apex.*—Acuminate.

*Base.*—Attenuate.

*Margin.*—Deeply serrated, "fern-like"; sinuses divergent.

*Length.*—Single leaves: About 7 cm. Compound leaves with three leaflets: About 12 cm. Compound leaves with five leaflets: About 16 cm.

*Width.*—Single leaves: About 4 cm. Compound leaves with three leaflets: About 8 cm. Compound leaves with five leaflets: About 12 cm.

*Venation pattern.*—Pinnate.

*Texture, upper and lower surfaces.*—Smooth, glabrous.

*Color.*—Developing leaves, upper surface: Close to 146B. Developing leaves, lower surface: Close to 147C. Fully expanded leaves, upper surface: Close to 146C; venation, close to 151A. Fully expanded leaves, lower surface: Close to 147B; venation, close to 146B.

*Petioles.*—Length: About 1.6 cm. Diameter: About 2 mm. Texture, upper and lower surfaces: Smooth, glabrous. Color, upper surface: Close to 147C. Color, lower surface: Close to 147D tinted with close to 61A.

Inflorescence description:

*Appearance/habit.*—Rotate decorative-type inflorescences with ray and disc florets developing acropetally on a receptacle; inflorescences positioned above the foliage on straight and strong peduncles; inflorescences face mostly upright; freely flowering habit with about 19 inflorescences per plant.

*Fragrance.*—None detected.

*Time to flower.*—Plants flower continuously during the summer and autumn in The Netherlands.

*Post-production longevity.*—Good postproduction longevity; inflorescences maintain good substance for about 25 days on the plant and for about ten days as a cut flower; inflorescences persistent.

*Inflorescence bud.*—Height: About 1.2 cm. Diameter: About 2.7 cm. Shape: Oblate. Color: Towards the base, close to 146C; mid-section and towards the apex, close to 153A.

*Inflorescence size.*—Diameter: About 14 cm. Depth (height): About 8 cm. Disc diameter: About 1.4 cm. Receptacle height: About 1.7 cm. Receptacle diameter: About 1.5 cm. Receptacle color: Close to 146A.

*Ray florets.*—Length: About 5.5 cm. Width: About 2.5 cm. Shape: Ovate. Apex: Obtuse. Base: Attenuate. Aspect: Initially upright to roughly perpendicular to the peduncle to reflexed. Texture, upper and lower surfaces: Smooth, glabrous; shiny. Number of ray florets per inflorescence: About 130 arranged in about 17 whorls. Color: When opening, upper surface: Close to 43A; longitudinal mid-section, close to 42A. When opening, lower surface: Towards the base, close to 7A; mid-section, close to 34A; towards the margins, close to 25A. Fully opened, upper surface:

Towards the base, close to 14A; mid-section and towards the apex and margins, close to 33A. Fully opened, lower surface: Close to 12A blushed with close to 33C.

*Disc florets.*—Shape: Tubular; apex dentate. Length: About 7 mm. Diameter: About 2 mm. Number of disc florets per inflorescence: About 25. Color, immature: Towards the base, close to 6C; mid-section, close to 17A; towards the apex, close to 154C. Color, mature: Towards the base, close to 1D; mid-section, close to 1C; towards the apex, close to 17A.

*Phyllaries.*—Quantity per inflorescence: About eight arranged in 1 to 1.5 whorls. Length: About 1.8 cm. Width: About 9 mm. Shape: Ovate, occasionally twisted. Apex: Acute. Base: Attenuate. Margin: Entire. Texture, upper and lower surfaces: Smooth, glabrous; shiny. Color, upper surface: Close to 146A; spots, close to 187A. Color, lower surface: Close to 146B.

*Peduncles.*—Length: Terminal peduncle: About 25 cm. Fourth peduncle: About 20 cm. Diameter: About 5 mm. Strength: Strong. Aspect: Erect to about 20° from vertical. Texture: Smooth, glabrous. Color: Close to 152A tinted with close to 187A.

*Reproductive organs.*—Androecium, present on disc florets: Quantity per disc floret: Five. Anther shape: Lanceolate. Anther length: About 2 mm. Anther color: Close to 17B. Pollen amount: Scarce. Pollen color: Close to 23A. Gynoecium, present on ray and disc florets: Quantity per ray or disc floret: One. Pistil length: About 4 mm. Stigma shape: Lanceolate. Stigma color: Close to 17A. Style length: About 3 mm. Style color: Close to 1D. Ovary color: Close to 166B. Fruits: Length: About 2.6 cm. Diameter: About 2.5 cm. Color: Close to 187B. Seeds: Length: About 8 mm. Diameter: About 2 mm. Color: Close to 199A.

Disease/pest resistance: Plants of the new *Dahlia* have not been shown to be resistant to pathogens and pests common to *Dahlia*.

Garden performance: Plants of the new *Dahlia* have exhibited good tolerance to rain and wind and have been observed to tolerate temperatures from about 0° C. to about 40° C.

It is claimed:

1. A new and distinct *Dahlia* plant named 'Karma Fiesta' as illustrated and described.

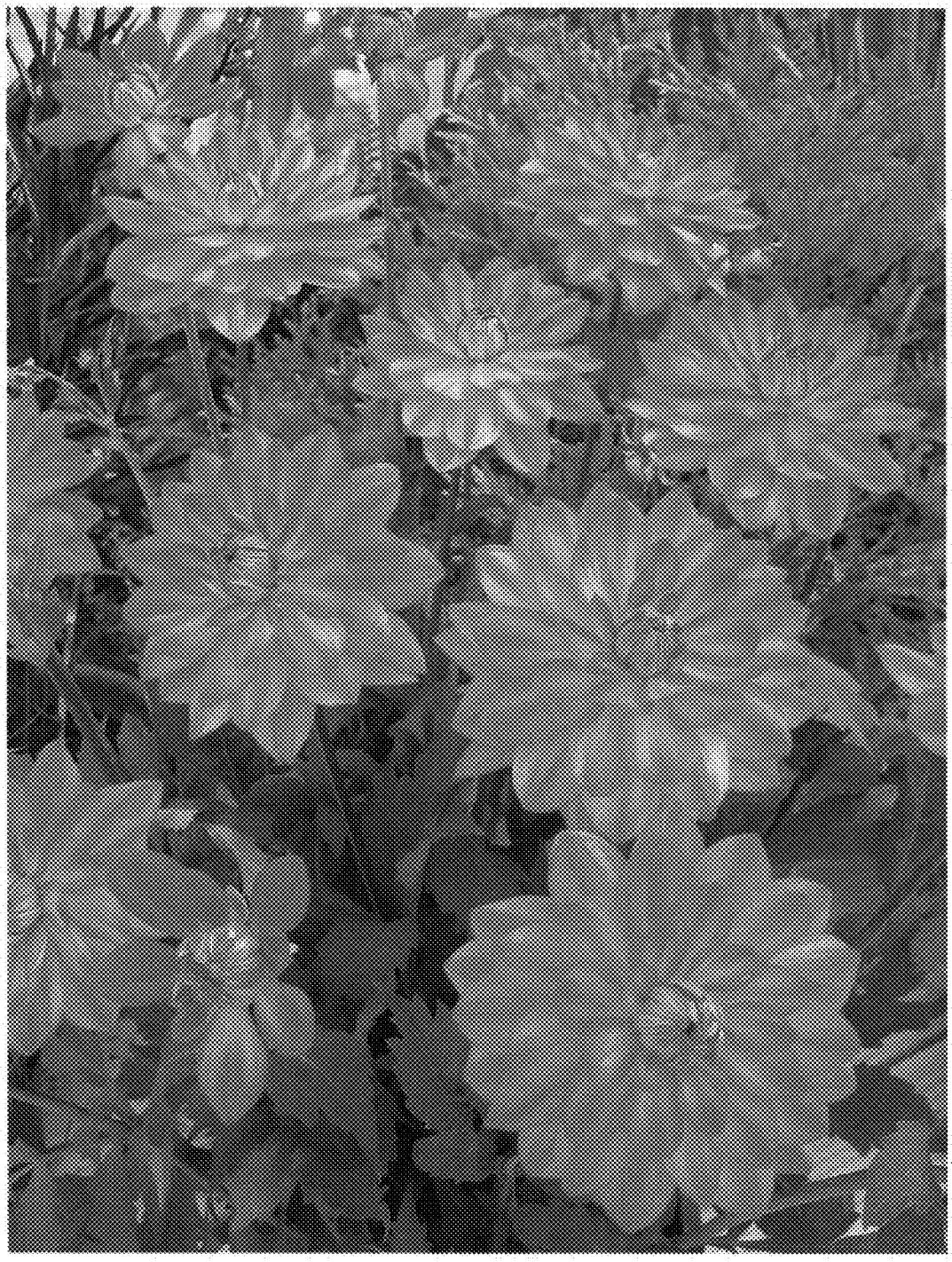

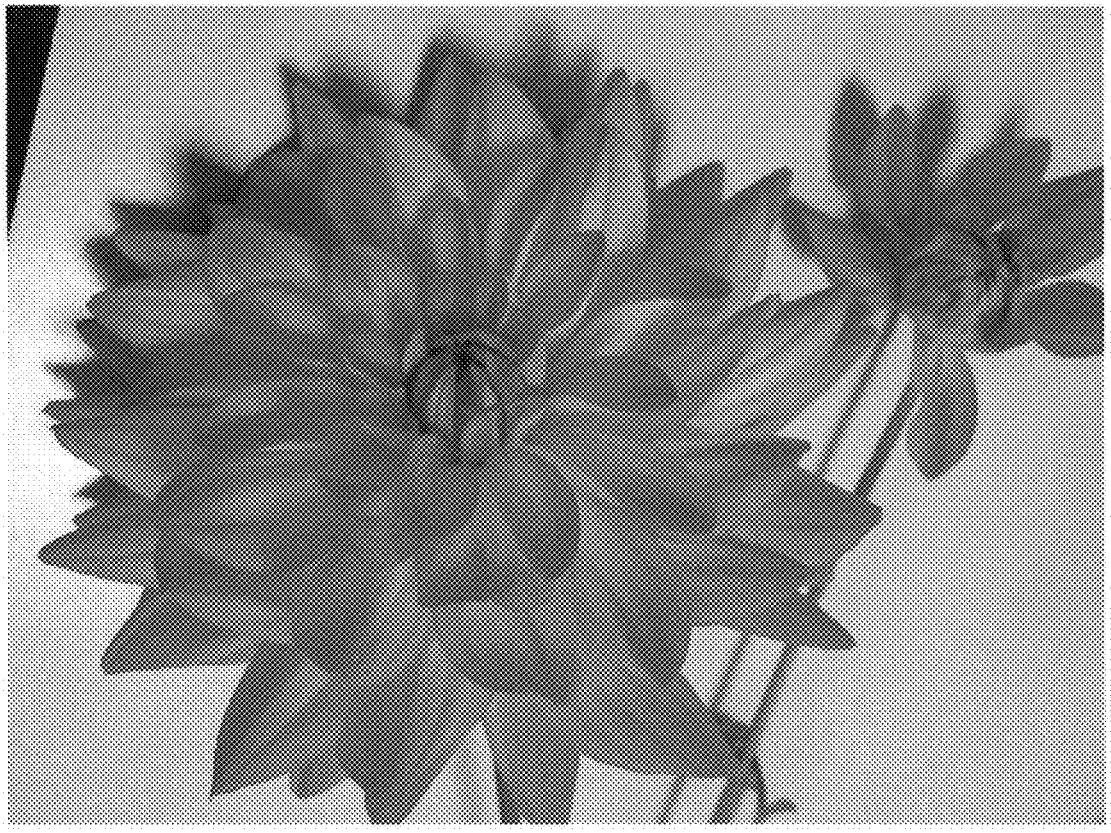

* * * * *